US006656456B2

(12) United States Patent
Dodd et al.

(10) Patent No.: US 6,656,456 B2
(45) Date of Patent: *Dec. 2, 2003

(54) SKIN DEODORIZING COMPOSITIONS

(75) Inventors: Michael Thomas Dodd, Florence, KY (US); Toan Trinh, Maineville, OH (US); Robert Gregory Bartolo, Montgomery, OH (US); Karl Shiqing Wei, Mason, OH (US); Mark Richard Sine, Morrow, OH (US); David Andrew Jakubovic, Staines (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/443,420

(22) Filed: Nov. 19, 1999

(65) Prior Publication Data

US 2002/0176879 A1 Nov. 28, 2002

Related U.S. Application Data

(63) Continuation of application No. 09/321,292, filed on May 27, 1999, now Pat. No. 6,344,218.
(60) Provisional application No. 60/109,602, filed on Nov. 23, 1998.

(51) Int. Cl.$^7$ .................................................. A61K 7/36
(52) U.S. Cl. ........................ 424/67; 424/401; 424/400; 424/65; 424/78.02; 424/78.03; 424/78.08; 424/78.17
(58) Field of Search ............................ 424/78.01, 76.8, 424/400, 401, 65, 67, 78.02, 78.03, 78.08, 78.17

(56) References Cited

U.S. PATENT DOCUMENTS

| | | | | | |
|---|---|---|---|---|---|
| 4,970,220 A | * | 11/1990 | Chaussee | ..................... | 514/358 |
| 5,593,670 A | | 1/1997 | Trinh et al. | ................. | 424/76.1 |
| 5,643,584 A | | 7/1997 | Farng et al. | ................. | 424/401 |
| 5,723,110 A | * | 3/1998 | Yamamoto et al. | ........... | 424/65 |
| 5,858,335 A | * | 1/1999 | Lucas et al. | .................. | 424/65 |
| 5,861,144 A | * | 1/1999 | Peterson et al. | ............... | 424/65 |
| 5,861,146 A | * | 1/1999 | Peterson et al. | ............... | 424/65 |
| 5,861,147 A | * | 1/1999 | Dodd et al. | ................... | 424/65 |
| 5,874,067 A | * | 2/1999 | Lucas et al. | ............... | 424/76.8 |
| 5,874,070 A | * | 2/1999 | Trinh et al. | .................... | 424/65 |
| 5,928,631 A | * | 7/1999 | Lucas et al. | .................. | 424/65 |
| 5,942,214 A | * | 8/1999 | Lucas et al. | ............... | 424/76.8 |

FOREIGN PATENT DOCUMENTS

| | | | | |
|---|---|---|---|---|
| EP | 0 701 813 A2 | 3/1996 | ............ | A61K/7/46 |
| WO | WO 94/12217 | 6/1994 | .......... | A61K/47/28 |
| WO | WO 97/10805 | 3/1997 | ............ | A61K/9/00 |
| WO | WO 98/26808 | 6/1998 | ............. | A61L/9/01 |
| WO | WO 98/27261 | 6/1998 | ............. | D06L/3/12 |
| WO | WO 98/47536 | 10/1998 | .......... | A61K/47/40 |
| WO | WO 98/56889 | 12/1998 | ............ | C11D/3/22 |
| WO | WO 98/56890 | 12/1998 | ............ | C11D/3/22 |

* cited by examiner

*Primary Examiner*—Thurman K. Page
*Assistant Examiner*—Liliana Di Nola-Baron
(74) *Attorney, Agent, or Firm*—John M. Howell; Marianne Dressman; Tara M. Rosnell

(57) ABSTRACT

The present invention relates to aqueous gel compositions comprising an odor controlling agent for deodorizing skin surfaces. Articles of manufacture and methods of deodorizing the skin using disclosed compositions are also disclosed.

26 Claims, No Drawings

SKIN DEODORIZING COMPOSITIONS

CROSS REFERENCE TO RELATED APPLICATIONS

This application claims the benefit of Provisional Application Serial No. 60/109,602, filed Nov. 23, 1998 (P&G Case 7357P) and is a continuation of U.S. Pat. No. 6,344,278, filed May 27, 1999 (P&G Case 7355R).

FIELD OF THE INVENTION

The present invention relates to aqueous gel compositions comprising an odor controlling agent for deodorizing skin surfaces. Articles of manufacture and methods of deodorizing the skin using disclosed compositions are also disclosed.

BACKGROUND OF THE INVENTION

Today's consumers are well acquainted with the notion of germs and germ transmission. Daily, people come into contact with germs at eating establishments, the gym, while changing diapers or using portable toilet facilities (e.g., portapotties). Once in contact with human hands, these germs (i.e., micro-organisms such as bacteria, fungus and/or viruses) are quickly passed from individual to individual and, thus, contribute to the spread of contagious and/or infectious diseases. One of the best and easiest ways of preventing such germ and/or disease transmission is by routinely and conscientiously wash one's hands. Recognizing the inconvenience or impossibility of such hand washing under certain traveling conditions and/or time constraints, a number of manufactures have introduced hand sanitizing products which sanitize skin surfaces without the need for water and/or towels.

Although current hand sanitizing products kill the germs associated with such routine activities as gasing up automobiles, changing diapers or handling exercise equipment, they can fail to eliminate their attendant malodors (e.g., gasoline odors). Moreover, malodor can arise from activities not normally associated with germ transmission (e.g., odors from food preparation such as onion, garlic etc.). Thus, the need exists for developing products which not only kill germs associated with daily activities but also which eliminate attendant malodor. The present inventors have found that aqueous, skin sanitizing compositions comprising select sanitizing agents and an odor controlling agent provide excellent antimicrobial activity as well as improved odor control.

Therefore, an important aspect of the present invention is to provide improved skin deodorizing compositions.

Another aspect of the present invention is to provide skin sanitizing compositions comprising an odor controlling component and select sanitizing agents.

These and other aspects will become readily apparent from the detailed description which follows.

SUMMARY OF THE INVENTION

The compositions of the present invention relate to stable, preferably translucent, more preferably clear, skin sanitizing and deodorizing compositions, comprising:

a.) an effective amount to provide odor control benefit of an odor controlling agent, preferably selected from the group consisting of cyclodextrin, water soluble metallic salt, zeolites, soluble carbonate and/or bicarbonate salts, water soluble ionic polymers, silica gel, silica molecular sieves, activated alumina, kieselguhr, fullers earth, montmorillonite, smectite, attapulgite, bentonite, palygorskite, kaolinite, illite, halloysite, hectorite, beidellite, nontronite, saponite, hormite, vermiculite, sepiolite, chlorophyll, soda lime, calcium oxide, chitin, potassium permanganate, activated charcoal or activated carbon, and mixtures thereof;

b.) an effective amount to provide sanitizing benefit of a select sanitizing agent prefably selected from the group consisting of an alcohol antiseptic an antimicrobial, and mixtures thereof;

c.) optionally, from 0 to about 10% of thickener;

d.) optionally, from 0 to about 10% of emollient;

f.) optionally, from 0 to about 1% of perfume; and g.) water.

In one aspect of the present invention, gel compositions are preferred. The present invention also relates to methods of using the personal cleansing compositions. The present invention further relates to an article of manufacture comprising the skin sanitizing and deodorizing composition incorporated into a preferably clear dispensing container.

One preferred skin sanitizing and deodorizing composition of the present invention comprises:

a.) an effective amount of an odor controlling agent to provide odor control benefit;

b.) from about 40% to about 99% of an alcohol antiseptic;

c.) optionally, from 0 to about 10% of a water-soluble metallic salt;

d.) optionally, from 0 to about 10% of a thickener;

e.) optionally, from 0 to about 10% of an emollient;

f.) optionally, from 0 to about 1% of perfume; and g.) water.

Another preferred skin sanitizing and deodorizing gel composition of the present invention comprises:

a.) an effective amount of odor controlling agent to provide odor control benefit;

b.) an effective amount of sanitizing agent comprising antimicrobial agent to kill or reduce the growth of microorganisms;

c.) from 0.01% to about 10% of thickener;

d.) optionally, from 0 to about 10% of emollient;

e.) optionally, from 0 to about 1% of perfume; and f.) water.

The present invention also relates to stable, preferably translucent, more preferably clear, skin deodorizing gel compositions, comprising:

a.) an effective amount of odor controlling agent to provide odor control benefit;

b.) from 0.01% to about 10% of thickener;

c.) optionally, from 0 to about 1% of perfume;

d.) optionally, from 0 to about 10% of emollient;

e.) optionally, from 0 to about 0.2% of antimicrobial preservative; and f.) water.

DETAILED DESCRIPTION OF THE INVENTION

The skin sanitizing and deodorizing compositions of the present invention can comprise, consist of, or consist essentially of the essential elements and limitations of the invention described herein, as well any of the additional or optional ingredients, components, or limitations described herein.

All percentages, parts and ratios are based upon the total weight of the personal cleansing compositions of the present invention, unless otherwise specified. All such weights as they pertain to listed ingredients are based on the active level and, therefore, do not include carriers or by-products that may be included in commercially available materials, unless otherwise specified.

By the term "alcohol antiseptic" as used herein, means an alcohol (or combination of alcohols) which is effective, at the concentration employed, to kill or reduce the growth of microorganisms, for example, bacteria, with which it comes in contact.

By the term "instant" as used herein means the compositions of the present invention disinfect the skin area within about 5 minutes, preferably within about 1 minute, more preferably within about 30 seconds, and even more preferably within about 20 seconds, without the need for soap and water.

The term "safe and effective amount" as used herein means an amount of a compound or composition sufficient to significantly induce a positive benefit, preferably an odor controlling and antimicrobial benefit, including independently the benefits disclosed herein, but low enough to avoid serious side effects, i.e., to provide a reasonable benefit to risk ratio, within the scope of sound judgment of the skilled artisan.

Preferably, the sanitizing and deodorizing composition of the present invention is clear. The term "clear" as defined herein means transparent or translucent, preferably transparent as in "water clear," when observed through a layer having a thickness of less than about 10 cm.

The skin sanitizing compositions of the present invention, including the essential and optional components thereof, are described in detail hereinafter.

Essential Components

Odor Controlling Agent

An essential ingredient of the present invention is the odor controlling agent. The phrase "odor controlling agent," as used herein, comprises material or materials which, individually or when formulated into the compositions of the present invention, serve to bind or entrap malodor molecules onto or into their molecular structures, or chemically react with malodor molecules such that the malodor molecule goes undetected by most (if not all) olfactory senses. Examples of suitable odor controlling agents include, but are not limited to, cyclodextrin, water soluble metallic salt, zeolites, soluble carbonate and/or bicarbonate salts, water soluble ionic polymers, silica gel, silica molecular sieves, activated alumina, kieselguhr, fullers earth, montmorillonite, smectite, attapulgite, bentonite, palygorskite, kaolinite, illite, halloysite, hectorite, beidellite, nontronite, saponite, hormite, vermiculite, sepiolite, chlorophyll, soda lime, calcium oxide, chitin, potassium permanganate, activated charcoal or activated carbon, and mixtures thereof, preferably cyclodextrin, water soluble metallic salt, soluble carbonate and/or bicarbonate salts, water soluble ionic polymers, zeolites and mixtures thereof, more preferably cyclodextrin, water soluble metallic salt, and mixtures thereof.

Also preferred for use herein are hydrolysates of keratin material and phosphoric diester compounds as described in U.S. Pat. Nos. 4,591,497 and 5,556,614, respectively; both patents are herein incorporated by reference in their entirety.

Deodorizing compositions such as that described in U.S. Pat. Nos. 4,818,524 and 4,946,672 are also preferred for use in the present compositions; both patents are herein incorporated by reference in their entirety.

Cyclodextrins

Preferred odor control agents include cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. The term "water-soluble, uncomplexed cyclodextrin" as used herein means uncomplexed cyclodextrin having a minimum solubility limit of 1% (1 gram in 100 grams of water).

Non-derivatised beta-cyclodextrin can be present at a level up to its solubility limit of about 1.85% at room temperature. When beta-cyclodextrin is applied to a wipe substrate, levels higher than its solubility limit can be used.

Highly water-soluble cyclodextrins are also preferred to be used in the present invention, such as, alpha-cyclodextrin and/or derivatives thereof, gamma-cyclodextrin and/or derivatives thereof, derivatised beta-cyclodextrins, and/or mixtures thereof. Highly water-soluble cyclodextrins are those having water solubility of at least about 10 g in 100 ml of water at room temperature, preferably at least about 20 g in 100 ml of water, more preferably at least about 25 g in 100 ml of water at room temperature. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl groups, such as hydroxypropyl cyclodextrins and/or hydroxyethyl cyclodextrins, wherein R is a —$CH_2$—CH(OH)—$CH_3$ or a —$CH_2CH_2$—OH group; those with (hydroxyalkyl)alkylenyl bridging groups such as cyclodextrin glycerol ethers wherein (2-hydroxyethyl)ethylenyl, —$CH_2$CH($CH_2$OH)—, groups bridge between the 2' and 3' hydroxyl oxygens on the glucosyl units; branched cyclodextrins such as maltose-bonded cyclodextrins; cationic cyclodextrins such as those containing 2-hydroxy-3-(dimethylamino) propyl ether, wherein R is $CH_2$—CH(OH)—$CH_2$—N($CH_3$)$_2$ which is cationic at low pH; quaternary ammonium, e.g., 2-hydroxy-3-(trimethylammonio)propyl ether chloride groups, wherein R is $CH_2$—CH(OH)—$CH_2$—N$^+$($CH_3$)$_3$Cl$^-$; anionic cyclodextrins such as carboxymethyl cyclodextrins, cyclodextrin sulfobutylethers, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, herein incorporated by reference; and mixtures thereof. Other cyclodextrin derivatives are disclosed in U.S. Pat. No. 3,426,011, Parmerter et al., issued Feb. 4, 1969; U.S. Pat. Nos. 3,453,257; 3,453,258; 3,453,259; and 3,453,260, all in the names of Parmerter et al., and all issued Jul. 1, 1969; U.S. Pat. No. 3,459,731, Gramera et al., issued Aug. U.S. Pat, No. 5, 1969; 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; U.S. Pat. No. 5,534,165, Pilosof et al., issued Jul. 9, 1996, all of said patents being incorporated herein by reference.

More preferred are alpha-cyclodextrin, beta-cyclodextrin, hydroxypropyl alpha-cyclodextrin, hydroxypropyl beta-cyclodextrin, methylated-alpha-cyclodextrin, methylated-beta-cyclodextrin, cyclodextrin glycerol ether, and mixtures thereof.

It is also preferable to use a mixture of cyclodextrins. Such mixtures absorb body malodors more broadly by complexing with a wider range of odoriferous molecules having a wider range of molecular sizes. The levels of cyclodextrin are from about 0.1% to about 5%, preferably from about 0.2% to about 4%, more preferably from about 0.3% to about 3%, most preferably from about 0.4% to about 2%, by weight of the composition.

Concentrated compositions can also be used. When a concentrated product is used, i.e., when the level of cyclodextrin used is from about 3% to about 5%, it is preferable to dilute the composition before applying to the skin in order to avoid tacky skin feel and/or an undesirable amount of residue. Preferably the cyclodextrin is diluted with about 50% to about 2000%, more preferably with about 60% to about 1000%, most preferably with about 75% to about 500%, by weight of the composition of water.

The complexation between cyclodextrin and odorous molecules occurs rapidly in the presence of water when the solubilized cyclodextrins are first applied to the skin. Thus, the availability of solubilized uncomplexed cyclodextrin is essential for an effective and efficient odor control performance.

It is also preferable to use a mixture of cyclodextrins. Such mixtures can complex with a wider range of odoriferous molecules having a wider range of molecular sizes. Preferably at least a portion of the cyclodextrins is alpha-cyclodextrin and its derivatives thereof, gamma-cyclodextrin and its derivatives thereof, and/or beta-cyclodextrin and its derivatives thereof, and mixtures thereof.

Cyclodextrins particularly preferred for use herein are alpha-cyclodextrin, beta-cyclodextrin, hydroxypropyl alpha-cyclodextrin, hydroxypropyl beta-cyclodextrin, methylated alpha-cyclodextrin, methylated beta-cyclodextrin, and mixtures thereof. More preferred for use herein are alpha-cyclodextrin, beta-cyclodextrin, hydroxypropyl beta-cyclodextrin, methylated beta-cyclodextrin, and mixtures thereof.

For reducing malodor impression on skin, the composition is preferably used as a hand gel or spray. Preferably, the composition is not discernible when dry. Typical levels of the odor controlling agent are from about 0.1% to about 10%, preferably from about 0.2% to about 4%, more preferably from about 0.3% to about 3%, most preferably from about 0.4% to about 2%, by weight of the composition.

Water Soluble Metallic Salts

Water soluble metallic salts are also preferred as odor control agent in the composition of the present invention. A water-soluble metallic salt can be present in the deodorizing composition of the present invention to absorb amine and sulfur-containing compounds. Furthermore, they usually do not contribute an odor of their own. Preferably the water-soluble metallic salts are selected from the group consisting of copper salts, zinc salts, and mixtures thereof.

The preferred zinc salts have been used most often for their ability to ameliorate malodor, e.g., in mouth wash products, as disclosed in U.S. Pat. No. 4,325,939, issued Apr. 20, 1982 and U.S. Pat. No. 4,469,674, issued Sept. 4, 1983, to N. B. Shah, et al., incorporated herein by reference. U.S. Pat. No. 3,172,817, issued to Leupold, et al., discloses deodorizing compositions containing slightly water-soluble salts of an acyl-acetone with a polyvalent metal, including copper and zinc salts. Said patents are incorporated herein by reference.

Examples of preferred water-soluble zinc salts are zinc chloride, zinc gluconate, zinc lactate, zinc maleate, zinc salicylate, zinc sulfate, etc. Highly-ionized and soluble zinc salts such as zinc chloride, provide the best source of zinc ions. Examples of preferred copper salts are copper chloride and copper gluconate. Preferred metallic salts are zinc chloride and copper chloride, more preferably zinc chloride.

Metallic salts are added to the composition of the present invention typically at a level of from about 0.01% to about 10%, preferably from about 0.2% to about 7%, more preferably from about 0.3% to about 5%, by weight of the composition. When zinc salts are used as the metallic salt, and a clear composition is desired, it is preferable that the pH of the solution is adjusted to less than about 7, more preferably less than about 6, most preferably, less than about 5, in order to keep the solution clear.

Soluble Carbonate and/or Bicarbonate Salts

Water-soluble alkali metal carbonate and/or bicarbonate salts, such as sodium bicarbonate, potassium bicarbonate, potassium carbonate, cesium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the present invention it is preferably that incompatible metal salts not be present in the invention. Preferably, when these salts are used the liquid composition should be essentially free of zinc and other incompatible metal ions, e.g., Ca, Fe, Ba, etc. which form water-insoluble salts.

Water-Soluble Ionic Polymers

Water-soluble anionic polymers, e.g., polyacrylic acids and their water-soluble salts are useful in the present invention to control certain amine-type odors. Preferred polyacrylic acids and their alkali metal salts have an average molecular weight of less than about 20,000, preferably less than 10,000, more preferably from about 500 to about 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990 to N. Kobayashi and A. Kawazoe, incorporated herein by reference. Another example of water-soluble polymers containing both cationic and anionic functionalities is a copolymer of dimethyldiallyl ammonium chloride and acrylic acid, commercially available under the trade name Merquat 280® from Calgon.

When a water-soluble polymer is used it is typically present at a level of from about 0.001% to about 3%, preferably from about 0.005% to about 2%, more preferably from about 0.01% to about 1%, and even more preferably from about 0.05% to about 0.5%, by weight of the usage composition.

Zeolites

A preferred class of zeolites is characterized as "intermediate" silicate/aluminate zeolites. The intermediate zeolites are characterized by $SiO_2/AlO_2$ molar ratios of less than about 10. Preferably the molar ratio of $SiO_2/AlO_2$ ranges from about 2 to about 10. The intermediate zeolites have an advantage over the "high" zeolites. The intermediate zeolites have a higher affinity for amine-type odors, they are more weight efficient for odor absorption because they have a larger surface area, and they are more moisture tolerant and retain more of their odor absorbing capacity in water than the high zeolites. A wide variety of intermediate zeolites suitable for use herein are commercially available as Valfor® CP301-68, Valfor® 300-63, Valfor® CP300-35, and Valfor® CP300-56, available from PQ Corporation, and the CBV100® series of zeolites from Conteka.

Zeolite materials marketed under the trade name Abscents® and Smellrite®, available from The Union Carbide Corporation and UOP are also preferred. These materials are typically available as a white powder in the 3–5 micron particle size range. Such materials are preferred over the intermediate zeolites for control of sulfur-containing odors, e.g., thiols, mercaptans.

Activated Carbon. The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

Mixtures of the above described odor controlling agents can also be used. Odor controlling agents having noticeable color such as activated carbon are not preferred for skin treatment, but can be used for deodorizing and/or sanitizing benefit on other surfaces where appearance is not important.

Sanitizing Agent

Sanitizing agents useful in the compositions of the present invention can effectively eliminate or reduce the growth of harmful microorganisms that exist on the treated surface. When an odor control agent is present, it is preferred that the sanitizing agent is compatible with the odor control agent, i.e., the sanitizing agent does not substantially bind, tie up, complex, interact and/or react with said odor control agent in a way that effectively reduces and/or eliminates the activity of either or both agents. When cyclodextrin is present, it is preferred that the sanitizing agent is cyclodextrin-compatible, i.e., it does not substantially complex with the cyclodextrin. Preferred sanitizing actives are selected from alcohol antiseptic, antimicrobial active, and mixtures thereof.

Alcohol Antiseptic. The compositions of the present invention can contain from about 40% to about 99%, more preferably from about 45% to about 90%, most preferably from about 50% to about 75%, and even more preferably from about 55% to about 70% of an alcohol antiseptic or mixtures thereof. Examples of suitable alcohol antiseptics include, but are not limited to, ethanol, n-propanol and isopropanol or mixtures thereof. Particularly preferred alcohol antiseptic for use herein is ethanol.

Antimicrobial Agent

Antimicrobial active is useful in providing sanitizing benefit herein. The antimicrobial active preferably should be compatible with the odor controlling agent. When cyclodextrin is present, the antimicrobial active is preferably cyclodextrin-compatible, i.e., not substantially forming complexes with the cyclodextrin in the composition. The free, uncomplexed antimicrobial, e.g., antibacterial, active provides an optimum antibacterial performance.

a.) Fast Acting Antimicrobial Agent

Fast acting antimicrobials are preferred for use in the present invention. The term "fast acting antimicrobial" as used herein, means the antimicrobial or antimicrobial combination is effective, at the concentration employed, to kill or inactivate microorganisms, for example, bacteria, viruses, or fungi, within about 5 minutes, preferably within about 1 minute, more preferably within about 30 seconds, and even more preferably within about 20 seconds. Examples of suitable fast acting antimicrobial agents include, but are not limited to, quaternary compounds such as benzalkonium chloride and benzethonium chloride, acetic acid solutions, glutaral, halazone, chlorophene, zinc pyrithione, thymol, thimerosal, hexachlorophene, mefenide, nonoxynol-9, octoxynol-9, salicylic acid, selenium sulfide, silver nitrate, silver sulfadiazine, zinc sulfate, hydrogen peroxide, cetylpeyridinium chloride, formaldehyde, gentian violet, hexylresocinol, biguanide compounds, such as chlorhexidine salts; phenol compound such as cresol; iodine compounds such as povidone-iodine; and pigment compounds such as acrinol, salts thereof and mixtures thereof.

Particularly preferred fast acting antimicrobial agents are biguanides and quaternary compounds. Biguanides can function as disinfectants/sanitizers as well as finish product preservatives, and are useful in the compositions of the present invention, including 1,1'-hexamethylene bis(5-(p-chlorophenyl)biguanide), commonly known as chlorhexidine, and its salts, e.g., with hydrochloric, acetic and gluconic acids. The digluconate salt is highly water-soluble, about 70% in water, and the diacetate salt has a solubility of about 1.8% in water. When chlorhexidine is used as a sanitizer in the present invention it is typically present at a level of from about 0.001% to about 0.4%, preferably from about 0.002% to about 0.3%, and more preferably from about 0.05% to about 0.2%, by weight of the composition. In some cases, a level of from about 1% to about 2% may be needed for virucidal activity. Other useful biguanide compounds include Cosmoci® CQ®, Vantocil® IB, including poly (hexamethylene biguanide) hydrochloride. Other useful cationic antimicrobial agents include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like.

A wide range of quaternary compounds can also be used as fast acting antimicrobial actives in compositions of the present invention. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Witco/Sherex), and Hyamine® (available from Lonza); (2) di($C_6$–$C_{14}$)alkyl di short chain ($C_{1-4}$ alkyl and/or hydroxyalkyl) quaternary such as Bardac® products of Lonza, (3) N-(3-chloroallyl) hexaminium chlorides such as Dowicide® and Dowicil® available from Dow; (4) benzethonium chloride such as Hyamine® 1622 from Rohm & Haas; (5) methylbenzethonium chloride represented by Hyamine® 10× supplied by Rohm & Haas, (6) cetylpyridinium chloride such as Cepacol chloride available from of Merrell Labs. Examples of the preferred dialkyl quaternary compounds are di($C_8$–$C_{12}$)dialkyl dimethyl ammonium chloride, such as didecyldimethylammonium chloride (Bardac 22), and dioctyldimethylammonium chloride (Bardac 2050). Typical concentrations for biocidal effectiveness of these quaternary compounds range from about 0.001% to about 0.8%, preferably from about 0.005% to about 0.3%, more preferably from about 0.01% to about 0.2%, and even more preferably from about 0.03% to about 0.1%, by weight of the composition.

Such fast acting antimicrobials are well known and more fully described in U.S. Pat. No. 4,163,800; U.S. Pat. No. 3,152,181; U.S. Pat. No. 5,780,064; and Remington's pharmaceutical Sciences, $17^{th}$ ed. (Alfonso R. Gennaro ed., 1985) pp. 1158–1169, all of which are herein incorporated by reference in their entirety.

b.) Cyclodextrin Compatible Antimicrobial Active

When cyclodextrin is present, preferred antimicrobial actives are those that are water-soluble and are effective at low levels. Water-soluble antimicrobial actives useful in the present invention are those that have a solubility in water of at least about 0.3 g per 100 ml of water, i.e., greater than about 0.3% at room temperature, preferably greater than about 0.5% at room temperature. Antimicrobial actives with a water-solubility of less than about 0.3% and a molecular structure that readily fits into the the structural cavity of the odor controlling agent, have a greater tendency to form inclusion complexes with the odor controlling agent, thus rendering the antimicrobial active and odor controlling agent less effective. Therefore, in the presence of cyclodextrin, many well known antimicrobial actives such as short chain alkyl esters of p-hydroxybenzoic acid, commonly known as parabens; N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan are not preferred, because they are relatively ineffective when used in conjunction with cyclodextrin. However, these antimicrobial actives with poor water solubility can be very effective in conjunction with some other odor cotrol agents, and are preferred in such cases.

Improved sanitization can be provided by the compositions of the present invention additionally containing antimicrobial materials, e.g., antibacterial halogenated compounds and aromatic alcohols, and mixtures thereof. Typical concentrations for biocidal effectiveness of these antimicrobial compounds range from about 0.001% to about 1%, preferably from about 0.005% to about 0.3%, more preferably from about 0.01% to about 0.2%, and even more preferably from about 0.03% to about 0.1%, by weight of the usage composition.

i.) Halogenated Compounds

Preferred antimicrobial actives for use in the present invention are halogenated compounds. Some non-limiting examples of halogenated compounds suitable for use in the present invention are:

5-bromo-5-nitro-1,3-dioxane, available under the trade name Bronidox L® from Henkel. Bronidox L® has a solubility of about 0.46% in water.

2-bromo-2-nitropropane-1,3-diol, available under the trade name Bronopol® from Inolex. Bronopol has a solubility of about 25% in water.

1,1'-hexamethylene bis(5-(p-chlorophenyl)biguanide), commonly known as chlorhexidine, and its salts, e.g., with acetic and gluconic acids can be used as a preservative in the present invention. The digluconate salt is highly water-soluble, about 70% in water, and the diacetate salt has a solubility of about 1.8% in water.

1,1,1-Trichloro-2-methylpropan-2-ol, commonly known as chlorobutanol, with water solubility of about 0.8%.

4,4'-(Trimethylenedioxy)bis-(3-bromobenzamidine) diisethionate, or dibromopropamidine, with water solubility of about 50%.

Mixtures of the preferred halogenated compounds can also be used as the antimicrobial active in the present invention.

ii.) Aromatic Alcohols

Some non-limiting examples of aromatic alcoholic antibacterial compounds suitable for use in the present invention are:

4,4'-diamidino-α,ω-diphenoxypropane diisethionate, commonly known as propamidine isethionate, with water solubility of about 16%; and 4,4'-diamidino-α, ω-diphenoxyhexane diisethionate, commonly known as hexamidine isethionate. Typical effective level of these salts is about 0.0002% to about 0.05% by weight of the usage composition.

Other examples are benzyl alcohol, with a water solubility of about 4%; 2-phenylethanol, with a water solubility of about 2%; and 2-phenoxyethanol, with a water solubility of about 2.67%; 2,4-dichlorobenzyl alcohol; 2-phenoxyethanol; phenoxyisopropanol; 3-(4-chlorophenoxy)-1,2-propane diol.

Mixtures of the preferred aromatic alcoholic compounds can also be used as the antimicrobial active in the present invention.

Mixtures of the above described sanitizing agents can also be used.

Water

The personal cleansing compositions of the present invention comprise from about 5% to about 70%, preferably from about 10% to about 50%, more preferably from about 20% to about 50%, by weight of water. Any suitable source of water can be used. Preferred for use herein is deionized water or distilled water.

Optional Components

Emollient

Optionally, but preferably, emollients can be added to the composition of the present invention. Suitable emollients include, but are not limited to, volatile and non-volatile silicone oils, highly branched hydrocarbons, and non-polar carboxylic acid and alcohol esters, and mixtures thereof. Nonlimiting examples of such emollients include petrolatum, mineral oil, micro-crystalline wax, polyalkene, paraffin, cerasin, ozokerite, polyethylene and perhydrosqualene, dimethicones, cyclomethicones, dimethiconols, alkyl siloxane, polymethylsiloxane and methylphenylpolysiloxane and mixtures thereof. Also useful herein are polyols such as polyethylene glycol. More preferred emollients are those that are compatible with the odor controlling agent. The term "compatible," as used herein, means that material should not substantially form complexes with the odor controlling agent. The phrase "substantially form complexes," as used herein, means to form complexes to the extent that the performance of the odor controlling agent is diminished or reduced. Emollients useful in the instant invention are further described in U.S. Pat. Nos. 5,783,536; 5,674,511; and 4,919,934, to Deckner et al., issued Apr. 24, 1990, all of which are herein incorporated by reference in their entirety.

Emollients can typically comprise in total from about 0.5% to about 50%, preferably from about 0.5% to about 25%, and more preferably from about 0.5% to about 10% by weight of the compositions useful in the present invention.

Thickener

Optionally, but preferably, thickeners can be added to the composition of the present invention. Thickener is used to prepare the preferred gel compositions of the present invention. A gel composition can be applied on a non-horizontal surface and retained in place without running. This way, more actives can be applied per surface area for a better and more efficacious performance on the targeted surface, as compared to non-gel low viscosity composition which cannot be effectively retained on non-horizontal targeted surface if more than a minimum amount of composition is applied. The thickener is an essential ingredient when a sanitizing and deodorizing composition of the current invention contains odor control agent particulates such as zeolite, silica molecular sieves, silica gel, alumina, kieselguhr, fullers earth, activated charcoal or activated carbon. The thickener helps to uniformly suspend and disperse the odor control agent particulates in the composition, and to consistently apply the composition on the target surface for an effective and efficacious sanitizing and deodorizing performance. Furthermore, a gel composition can retain the volatile alcohol antiseptic better, to provide a longer lasting and more effective performance.

The thickener useful in the present invention should be compatible with the odor controlling agent The binding and/or interaction between the thickener and the odor controlling agent can diminish both the ability of the odor controlling agent to absorb odors and the ability of the thickener to provide high viscosity. When cyclodextrin is present, the preferred thickener is cyclodextrin-compatible, i.e., not complexing with the cyclodextrin. Examples of suitable thickeners include, but are not limited to, naturally-occurring polymeric materials such as sodium alginate, xanthan gum, quince seed extract, tragacanth gum, starch and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyacrylic acid, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminium silicates, such as, for example, bentonites. Thickeners which can complex with cyclodextrin, such as polyethylene glycol stearate and distearate, are not preferred in cyclodextrin-containing compositions.

Also useful herein are hydrophilic gelling agents such as the acrylic acid/ethyl acrylate copolymers and the carboxyvinyl polymers sold by the B.F. Goodrich Company under the trademark of Carbopol® resins. These resins consist essentially of crosslinked polyacrylic acid in the form of colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name, Carbopol Ultrez 10, Carbopol ETD2020, Carbopol 1382, and Carbopol 1342. Combination of the above polymers are also useful herein. Materials which can complex with cyclodextrin, such as Pemulen TR 1, are not preferred.

Hydrophobically modified celluloses are also suitable for use herein. These celluloses are described in detail in U.S. Pat. Nos. 4,228,277 and 5,104,646, both of which are herein incorporated by reference in their entirety.

Preferred for use herein are carbomers such as Carbopol 980, Carbopol 940, Carbopol Ultrez 10, Carbopol ETD2020 and mixtures thereof.

Mixtures of the above described thickeners can also be used. The thickener is preferably present at a concentration of from about 0.01% to about 10%, preferably from about 0.1% to about 5%, more preferably from about 0.1% to about 1% and even more preferably from about 0.1% to about 0.5%. Mixtures of the above thickeners may also be used.

Low Molecular Weight Polyols

Low molecular weight polyols with relatively high boiling points, as compared to water, such as ethylene glycol, diethylene glycol, propylene glycol and/or glycerol are preferred optional ingredients for improving odor control performance of the composition of the present invention.

It is believed that the polyols form ternary complexes with the odor controlling agents (e.g., cyclodextrin) and some malodorous molecules to improve their odor controlling properties. Preferably the glycol used is glycerin, ethylene glycol, propylene glycol, dipropylene glycol or mixtures thereof, more preferably ethylene glycol and propylene glycol. When used herein, cyclodextrins prepared by processes that result in a level of such polyols are highly desirable, since they can be used without removal of the polyols.

Typically, glycol is added to the composition of the present invention at a level of from about 0.01% to about 3%, by weight of the composition, preferably from about 0.05% to about 1%, more preferably from about 0.1% to about 0.5%, by weight of the composition. The preferred weight ratio of low molecular weight polyol to odor controlling agent is from about 2:1,000 to about 20:100, more preferably from about 3:1,000 to about 15:100, even more preferably from about 5:1,000 to about 10:100, and most preferably from about 1:100 to about 7:100. Mixtures of the above described polyols can also be used.

Crystal-Preventing or Inhibiting Agents

The compositions of the present invention preferably also contain crystal preventing or inhibiting agents. The term "crystal preventing or inhibiting agent," as used herein, refers to compounds or chemical entities which reduce and/or arrest the crystallization of cyclodextrin. Such crystallization tends to negatively affect product aesthetics and/or stability. Suitable crystal preventing or inhibiting agents include, but are not limited to, sugars, nonionic polymers and mixtures thereof.

Preferred crystal-preventing or inhibiting agents include sugars. Examples of suitable sugars include mono saccharides such as glucose, galactose, xylose, fructose, altose, altrose, tallose, mannose, arabinose, idose, lyxose, reose, ribose, allose, gulose, erythrose, threose, tagatose, sorbose, psicose, pentose, xylulose, ribulose, erythrulose, fucose, rhamnose, and a mixture thereof; disaccharide such as maltose, maltodextrin, isomaltose, lactose, xylobiose, gentiobiose, kojiobiose, cellobiose, sohorose, nigerose, sucrose, melibiose, laminaribiose, rutinose, lactulose, palatinose, turanose, trehalose and a mixture thereof; or trisaccharides such as maltotriose, meleziose, raffinose, glyceraldehyde, and a mixture thereof; furthermore oligosaccharides and derivatives thereof such as isomaltooligosaccharide are also useful as well as higher polysaccharides such as polydextrose; and also a mixture of the monosaccharide, disaccharide, trisaccharide, oligosaccharide and higher polysaccharide can be used for this purpose. Preferably, the oligosaccharide of the present invention contain from 2 to 10, more preferably, from 3 to 7, most preferably, from 3 to 6 saccharide units. Polysaccharides preferably contain from about 10 to about 1,000, more preferably, from 10 to 100, and most preferably, from 10 to 50 saccharide units. When used herein, the sugar preferably comprises from about 0.001% to about 10%, more preferably, from about 0.01% to about 1%, most preferably, from about 0.01% to about 0.5% of the present invention.

Alternatively, the crystal-preventing or inhibiting agent can be a nonionic polymer. Suitable nonionic polymers include, but are not limited to, cellulose ethers (e.g., hydroxybutyl methylcellulose, hydroxypropylcellulose, hydroxypropyl methylcellulose, ethylhydroxy ethylcellulose and hydroxyethylcellulose), propylene glycol alginates, polyacrylamide, guar gum, hydroxypropyl guar gum, locust bean gum, amylose, hydroxyethyl amylose, starch and starch derivatives and mixtures thereof. Preferred nonionic polymers include hydroxyethyl cellulose, hydroxypropyl cellulose, ethylhydroxyethyl cellulose, dextran, hydroxypropyl guar or mixtures thereof. When used herein, the nonionic polymer preferably comprises from about 0.001% to about 1%, more preferably, from about 0.01% to about 1%, most preferably, from about 0.01% to about 0.5% of the present invention.

Mixtures of the above may also be used.

Technical grades of cyclodextrin typically contain low levels of oligosaccharides and starch. For this reason, these grades of cyclodextrin are preferred for use in the present invention. Technical grades preferred for use herein include Technical Grade Alpha-Cyclodextrin (Alpha W 6 Technical Grade, supplied by Wacker Biochem Corporation, Adrian, Mich., U.S.A.), Technical Grade Beta Cyclodextrin (Beta W 7 Technical Grade, supplied by Wacker Biochem Corporation, Adrian, Mich., U.S.A.), Technical Grade Hydroxypropyl Beta Cyclodextrin (Beta W 7 HP Technical Grade, supplied by Wacker Biochem Corporation, Adrian, Mich., U.S.A.), and Technical Grade Methylated Beta Cyclodextrin (Beta W 7 M 1.8 Technical Grade, supplied by Wacker Biochem Corporation, Adrian, Mich., U.S.A.) and mixtures thereof. Such technical grade cyclodextrins can also be obtained from Cerestar, Hammond, Ind., U.S.A.

Skin Sensates

The skin sanitizing compositions of the present invention may also contain sensates.

When used in the present invention, sensates can be present at a level of from about 0.01% to about 10%, typically from about 0.1% to about 5%, and preferably from about 0.2% to about 1%. The level is selected to provide the desired level of consumer perceived sensation and can be modified as desired. Suitable sensate technologies include menthol, eucalyptus, 3-1-menthoxy propane-1,2-diol, N-substituted-p-menthane-3-carboxamides, acyclic carboxamides and mixtures thereof.

3-1-menthoxy propane 1,2-diol is fully described in detail in U.S. Pat. No. 4,459,425, issued Jul. 10, 1984 to Amano et. al, incorporated herein by reference in its entirety. This volatile aromatic is commercially available, being sold by Takasago Perfumery Co., Ltd., Tokyo, Japan.

The N-substituted-p-menthane-3-carboxamides are fully described in U.S. Pat. No. 4,136,163 to Watson et al., issued Jan. 23, 1979 incorporated herein by reference in its entirety. The most preferred volatile aromatic of this class is N-ethyl-p-menthane-3-carboxamide which is commercially available as WS-3 from Wilkinson Sword Limited.

Useful acyclic carboxamides are fully described in U.S. Pat. No. 4,230,688 to Rowsell et al., issued Oct. 28, 1980 incorporated herein by reference in its entirety. The most preferred volatile aromatic of this class is N,2,3-trimethyl-2-isopropylbutanamide which is commercially available as WS-23 from Wilkinson Sword Limited.

Perfume

The skin sanitizing and deodorizing compositions of the present invention can optionally provide a "scent signal" in the form of a pleasant odor which signals the removal of malodor. When perfume is added as a scent signal, it is added only at very low levels, e.g., from about 0% to about 0.5%, preferably from about 0.001% to about 0.3%, more preferably from about 0.005% to about 0.2%, even more preferably from about 0.01% to about 0.1%, by weight of the sanitizing composition.

Perfume can also be added to provide a more intense odor in product and on skin. When stronger levels of perfume are preferred, relatively higher levels of perfume can be added, e.g., up to about 1%, by weight of the sanitizing composition. Any type of perfume can be incorporated into the composition of the present invention. Suitable perfumes are described in U.S. Pat. No. 5,723,420, herein incorporated in its entirety.

When cyclodextrin is present, it is preferred that the perfume is cyclodextrin-compatible in the composition of the present invention. The perfume is compatible with odor controlling agent when it is added at a level wherein even if all of the perfume in the composition were to complex and/or bind/interact with the odor controlling agent, there will still be an effective level of odor controlling agent present in the solution to provide adequate odor control. In order to reserve an effective amount of odor controlling agent for odor control, perfume is typically present at a level wherein less than about 90% of the odor controlling agent complexes with the perfume, preferably less than about 50%, more preferably, less than about 30%, and most preferably, less than about 10%. The odor controlling agent to perfume weight ratio should be greater than about 8:1, preferably greater than about 10:1, more preferably greater than about 20:1, even more preferably greater than 40:1 and most preferably greater than about 70:1.

Hydrophilic perfume ingredients are preferred perfume ingredients when cyclodextrin is present. The hydrophilic perfume ingredients are more water soluble and have less of a tendency to complex with cyclodextrin. The degree of hydrophilicity of a perfume ingredient can be correlated with its octanol/water partition coefficient P. The octanol/water partition coefficient of a perfume ingredient is the ratio between its equilibrium concentration in octanol and in water. A perfume ingredient with a greater partition coefficient P is considered to be more hydrophobic. Conversely, a perfume ingredient with a smaller partition coefficient P is considered to be more hydrophilic. Since the partition coefficients of the perfume ingredients normally have high values, they are more conveniently given in the form of their logarithm to the base 10, logP. Thus the preferred perfume hydrophilic perfume ingredients of this invention have logP of about 3.5 or smaller, preferably of about 3.0 or smaller.

The logP of many perfume ingredients have been reported; for example, the Pomona92 database, available from Daylight Chemical Information Systems, Inc. (Daylight CIS), Irvine, Calif., contains many, along with citations to the original literature. However, the logP values are most conveniently calculated by, e.g., the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are used instead of the experimental logP values in the selection of perfume ingredients which are useful in the present invention.

Non-limiting examples of the more preferred hydrophilic perfume ingredients are allyl amyl glycolate, allyl caproate, amyl acetate, amyl propionate, anisic aldehyde, anisyl acetate, anisole, benzaldehyde, benzyl acetate, benzyl acetone, benzyl alcohol, benzyl formate, benzyl iso valerate, benzyl propionate, beta gamma hexenol, calone, camphor gum, laevo-carveol, d-carvone, laevo-carvone, cinnamic alcohol, cinnamyl acetate, cinnamic alcohol, cinnamyl formate, cinnamyl propionate, cis-jasmone, cis-3-hexenyl acetate, coumarin, cuminic alcohol, cuminic aldehyde, Cyclal C, cyclogalbanate, dihydroeuginol, dihydro isojasmonate, dimethyl benzyl carbinol, dimethyl benzyl carbinyl acetate, ethyl acetate, ethyl aceto acetate, ethyl amyl ketone, ethyl anthranilate, ethyl benzoate, ethyl butyrate, ethyl cinnamate, ethyl hexyl ketone, ethyl maltol, ethyl-2-methyl butyrate, ethyl methylphenyl glycidate, ethyl phenyl acetate, ethyl salicylate, ethyl vanillin, eucalyptol, eugenol, eugenyl acetate, eugenyl formate, eugenyl methyl ether, fenchyl alcohol, flor acetate (tricyclo decenyl acetate), fructone, frutene (tricyclo decenyl propionate), geraniol, geranyl oxyacetaldehyde, heliotropin, hexenol, hexenyl acetate, hexyl acetate, hexyl formate, hinokitiol, hydratropic alcohol, hydroxycitronellal, hydroxycitronellal diethyl acetal, hydroxycitronellol, indole, isoamyl alcohol, iso cyclo citral, isoeugenol, isoeugenyl acetate, isomenthone, isopulegyl acetate, isoquinoline, keone, ligustral, linalool, linalool oxide, linalyl formate, lyral, menthone, methyl acetophenone, methyl amyl ketone, methyl anthranilate, methyl benzoate, methyl benzyl acetate, methyl cinnamate, methyl dihydrojasmonate, methyl eugenol, methyl heptenone, methyl heptine carbonate, methyl heptyl ketone, methyl hexyl ketone, methyl isobutenyl tetrahydropyran, methyl-N-methyl anthranilate, methyl beta naphthyl ketone, methyl phenyl carbinyl acetate, methyl salicylate, nerol, nonalactone, octalactone, octyl alcohol (octanol-2), para-anisic aldehyde, para-cresol, para-cresyl methyl ether, para hydroxy phenyl butanone, para-methoxy acetophenone, para-methyl acetophenone, phenoxy ethanol, phenoxyethyl propionate, phenyl acetaldehyde, phenylacetaldehyde diethyl ether, phenylethyl oxyacetaldehyde, phenyl ethyl acetate, phenyl ethyl alcohol, phenyl ethyl dimethyl carbinol, prenyl acetate, propyl butyrate, pulegone, rose oxide, safrole, terpineol, vanillin, viridine, and mixtures thereof.

Nonlimiting examples of other preferred hydrophilic perfume ingredients which can be used in perfume compositions of this invention are allyl heptoate, amyl benzoate, anethole, benzophenone, carvacrol, citral, citronellol, citronellyl nitrile, cyclohexyl ethyl acetate, cymal, 4-decenal, dihydro isojasmonate, dihydro myrcenol, ethyl methyl phenyl glycidate, fenchyl acetate, florhydral, gamma-nonalactone, geranyl formate, geranyl nitrile, hexenyl isobutyrate, alpha-ionone, isobornyl acetate, isobutyl benzoate, isononyl alcohol, isomenthol, para-isopropyl phenylacetaldehyde, isopulegol, linalyl acetate, 2-methoxy naphthalene, menthyl acetate, methyl chavicol, musk ketone, beta naphthol methyl ether, neral, nonyl aldehyde, phenyl heptanol, phenyl hexanol, terpinyl acetate, Veratrol, yara—yara, and mixtures thereof.

Low Odor Detection Threshold Perfume Ingredient

The odor detection threshold of an odorous material is the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalari, editor, ASTM Data Series DS 48A, American Society for Testing and Materials, 1978, both of said publications being incorporated by reference. The use of small amounts of perfume ingredients that have low odor detection threshold values can improve perfume odor character, even though they are not as hydrophilic as perfume ingredients of group (a) which are given hereinabove. Perfume ingredients that do not belong to group (a) above, but have a significantly low detection threshold, useful in the composition of the present invention, are selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof. These materials are preferably present at low levels in addition to the hydrophilic ingredients of group (a), typically less than about 20%, preferably less than about 15%, more preferably less than about 10%, by weight of the total perfume compositions of the present invention. However, only low levels are required to provide an effect.

There are also hydrophilic ingredients of group (a) that have a significantly low detection threshold, and are especially useful in the composition of the present invention. Examples of these ingredients are allyl amyl glycolate, anethole, benzyl acetone, calone, cinnamic alcohol, coumarin, cyclogalbanate, Cyclal C, cymal, 4-decenal, dihydro isojasmonate, ethyl anthranilate, ethyl-2-methyl butyrate, ethyl methylphenyl glycidate, ethyl vanillin, eugenol, flor acetate, florhydral, fructone, frutene, heliotropin, keone, indole, iso cyclo citral, isoeugenol, lyral, methyl heptine carbonate, linalool, methyl anthranilate, methyl dihydrojasmonate, methyl isobutenyl tetrahydropyran, methyl beta naphthyl ketone, beta naphthol methyl ether, nerol, para-anisic aldehyde, para hydroxy phenyl butanone, phenyl acetaldehyde, vanillin, and mixtures thereof. Use of low odor detection threshold perfume ingredients minimizes the level of organic material that is released into the atmosphere.

Mixtures of the above described perfumes can also be used.

Surfactant

The optional surfactant provides a low surface tension that permits the composition to spread readily and more uniformly on skin surfaces and other surfaces and improve cleaning. The surfactant for use in the composition of the present invention should be compatible with the odor controlling agent. Nonlimiting examples of surfactants suitable for use in the present invention in the presence of cyclodextrin include, but are not limited to, selected silicone surfactants and block copolymers of ethylene oxide and propylene oxide.

Silicone Surfactant

A preferred class of surfactants are the polyalkylene oxide polysiloxanes having a dimethyl polysiloxane hydrophobic moiety and one or more hydrophilic polyalkylene side chains, and having the general formula:

$$R^1\text{—}(CH_3)_2SiO\text{—}[(CH_3)_2SiO]_a\text{—}[(CH_3)(R^1)SiO]_b\text{—}Si(CH_3)_2\text{—}R^1$$

wherein a+b are from about 1 to about 50, preferably from about 3 to about 30, more preferably from about 10 to about 25, and each $R^1$ is the same or different and is selected from the group consisting of methyl and a poly(ethyleneoxide/propyleneoxide) copolymer group having the general formula:

$$\text{—}(CH_2)_nO(C_2H_4O)_c(C_3H_6O)_dR^2$$

with at least one $R^1$ being a poly(ethyleneoxide/propyleneoxide) copolymer group, and wherein n is 3 or 4, preferably 3; total c (for all polyalkyleneoxy side groups) has a value of from 1 to about 100, preferably from about 6 to about 100; total d is from 0 to about 14, preferably from 0 to about 3; and more preferably d is 0; total c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group. Each polyalkylene oxide polysiloxane has at least one $R^1$ group being a poly(ethyleneoxide/propyleneoxide) copolymer group.

Nonlimiting examples of this type of surfactants are the Silwet® surfactants which are available OSi Specialties, Inc., Danbury, Conn. Representative Silwet surfactants are as follows.

| Name | Average MW | Average a + b | Average total c |
|------|------------|---------------|------------------|
| L-7608 | 600 | 1 | 9 |
| L-7607 | 1,000 | 2 | 17 |
| L-77 | 600 | 1 | 9 |
| L-7605 | 6,000 | 20 | 99 |
| L-7604 | 4,000 | 21 | 53 |
| L-7600 | 4,000 | 11 | 68 |
| L-7657 | 5,000 | 20 | 76 |
| L-7602 | 3,000 | 20 | 29 |

The molecular weight of the polyalkyleneoxy group $R^1$) is less than or equal to about 10,000. Preferably, the molecular weight of the polyalkyleneoxy group is less than or equal to about 8,000, and most preferably ranges from about 300 to about 5,000. Thus, the values of c and d can be those numbers which provide molecular weights within these ranges. However, the number of ethyleneoxy units ($\text{—}C_2H_4O$) in the polyether chain ($R^1$) must be sufficient to render the polyalkylene oxide polysiloxane water dispersible or water soluble. If propyleneoxy groups are present in the polyalkylenoxy chain, they can be distributed randomly in the chain or exist as blocks. Preferred Silwet surfactants are L-7600, L-7602, L-7604, L-7605, L-7622, L-7657, and mixtures thereof. Besides surface activity, polyalkylene oxide polysiloxane surfactants can also provide other benefits, such as lubricity and skin softness.

Block Polyoxyethylene-Polyoxypropylene Polymeric Surfactants

Suitable block polyoxyethylene-polyoxypropylene polymeric surfactants, that are compatible with most odor controlling agents, e.g., cyclodextrin, include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with certain odor controlling agents (e.g., cyclodextrin). Certain of the block polymer surfactant compounds designated Pluronic® and Tetronic® by the BASF-Wyandotte Corp., Wyandotte, Mich., are readily available.

Nonlimiting examples of suitable surfactants of this type include:

Pluronic Surfactants with the general formula $H(EO)_n(PO)_m(EO)_nH$, wherein EO is an ethylene oxide group, PO is a propylene oxide group, and n and m are numbers that indicate the average number of the groups in the surfactants.

Typical examples of Pluronic surfactants are:

| Name | Average MW | Average n | Average m |
|------|------------|-----------|-----------|
| L-101 | 3,800 | 4 | 59 |
| L-81 | 2,750 | 3 | 42 |
| L-44 | 2,200 | 10 | 23 |
| L-43 | 1,850 | 6 | 22 |
| F-38 | 4,700 | 43 | 16 |
| P-84 | 4,200 | 19 | 43, | and mixtures thereof.

Tetronic Surfactants with the general formula:

wherein EO, PO, n, and m have the same meanings as above. Typical examples of Tetronic surfactants are:

| Name | Average MW | Average n | Average m |
|------|------------|-----------|-----------|
| 901 | 4,700 | 3 | 18 |
| 908 | 25,000 | 114 | 22, | and mixtures thereof.

"Reverse" Pluronic and Tetronic surfactants have the following general formulas:

Reverse Pluronic Surfactants $H(PO)_m(EO)_n(PO)_mH$

Reverse Tetronic Surfactants

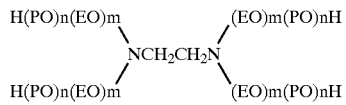

wherein EO, PO, n, and m have the same meanings as above.

Typical examples of Reverse Pluronic and Reverse Tetronic surfactants are:

| Name | Average MW | Average n | Average m |
|---|---|---|---|
| Reverse Pluronic surfactants: | | | |
| 10 R5 | 1,950 | 8 | 22 |
| 25 R1 | 2,700 | 21 | 6 |
| Reverse Tetronic surfactants | | | |
| 130 R2 | 7,740 | 9 | 26 |
| 70 R2 | 3,870 | 4 | 13 | and mixtures thereof.

Also useful are emulsifying surfactants selected from the group consisting of: emulsifying surfactants having an HLB value below 12 or about 12, preferably, from about 3 to below 12 or about 12, most preferably, from about 3 to about 11 such as steareth-2, PEG-5 soya sterol oil, PEG-10 soya sterol oil, diethanolamine cetyl phosphate, sorbitan monostearate (Span 60), diethyleneglycol monostearate, glyceryl monostearate, and mixtures thereof, emulsifying surfactants having an HLB value of 12 or above (or about 12 and above) such as Steareth-21, polyoxyethylene sorbitan tristearate (Tween 65), polyethylene glycol 20 sorbitan monostearate, polyethylene glycol 60 sorbitan monostearate, polyethylene glycol 80 sorbitan monostearate, Steareth-20, Ceteth-20, PEG-100 stearate, sodium stearoyl sarcosinate, hydrogenated lecithin, sodium cocoylglyceryl sulfate, sodium stearyl sulfate, sodium stearoyl lactylate, PEG-20 methyl glucoside sesquistearate, PEG-20 glyceryl monostearate, sucrose monostearate, sucrose polystearates (having a high proportion of sucrose monostearate), polyglyceryl 10 stearate, polyglyceryl 10 myristate, steareth 10, DEA oleth 3 phosphate, DEA oleth 10 phosphate, PPG-5 Ceteth 10 phosphate sodium salt, PPG-5 Ceteth 10 phosphate potassium salt, and mixtures thereof; and mixtures thereof. Preferably, the compositions of the present invention comprise at least one emulsifying surfactant having an HLB value below 12 (or below about 12) and at least one emulsifying surfactant having an HLB value of 12 or above (or about 12 or above). "HLB" is well known to one of ordinary skill in the art and means hydrophobic lipophilic balance. See, "The HLB System, A Time-Saving Guide to Emulsifier Selection," ICI Americas Inc., August (1984) and McCutcheon's, Detergents and Emulsifiers, North American Edition (1987), published by Mc Publishing Co.; which list various emulsifiers useful herein. Both of these references are incorporated herein by reference in their entirety.

The emulsifying surfactant comprises from about 0% to about 20%, preferably from about 0.1% to 10%, more preferably, from about 0.25% to about 5%, most preferably, from about 0.25% to about 2.5%.

Other useful surfactants are disclosed in U.S. Pat. No. 5,783,200, herein incorporated by reference in its entirety.

Mixtures of the above described surfactants can also be used. Typical levels of surfactants in the skin sanitizing and odor control compositions are from about 0.01% to about 5%, preferably from about 0.03% to about 2%, more preferably from about 0.05% to about 1%, by weight of the composition.

Optional Preservative

Optionally, solubilized, water-soluble, antimicrobial preservative can be added to the composition of the present invention if the sanitizing agent is not sufficient, or is not present, to provide adequate preservative activity. Such additional preservative activity is particularly useful when using certain organic odor controlling agents, especially cyclodextrins—compounds of varying numbers of glucose units—which can become prime breeding ground for certain microorganisms, especially when in aqueous compositions.

It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives with complimentary and/or supplementary activity. A mixture of broad spectrum preservatives can also be used. In some cases where a specific group of microbial contaminants is problematic (such as Gram negatives), aminocarboxylate chelators may be used alone or as potentiators in conjunction with other preservatives. These chelators which include, e.g., ethylenediaminetetraacetic acid (EDTA), hydroxyethylenediaminetriacetic acid, diethylenetriaminepentaacetic acid, and other aminocarboxylate chelators, and mixtures thereof, and their salts, and mixtures thereof, can increase preservative effectiveness against Gram-negative bacteria, especially Pseudomonas species.

Antimicrobial preservatives useful in the present invention include biocidal compounds, i.e., substances that kill microorganisms, or biostatic compounds, i.e., substances that inhibit and/or regulate the growth of microorganisms.

Preferred antimicrobial preservatives are those that are water-soluble and are effective at low levels because the organic preservatives can form inclusion complexes with the cyclodextrin molecules and compete with the malodorous molecules for the cyclodextrin cavities, thus rendering the cyclodextrins ineffective as odor controlling actives. Water-soluble preservatives useful in the present invention are those that have a solubility in water of at least about 0.3 g per 100 ml of water, i.e., greater than about 0.3% at room temperature, preferably greater than about 0.5% at room temperature.

Typical levels of preservative are from about 0.0002% to about 0.2%, preferably from about 0.0003% to about 0.1%, by weight of the composition.

Preferred water-soluble preservatives include organic sulfur compounds, halogenated compounds, cyclic organic nitrogen compounds, low molecular weight aldehydes, quaternary ammonium compounds, dehydroacetic acid, phenyl and phenolic compounds, and mixtures thereof.

The following are non-limiting examples of preferred water-soluble preservatives for use in the present invention.

Organic Sulfur Compounds

Preferred water-soluble preservatives for use in the present invention are organic sulfur compounds. Some non-limiting examples of organic sulfur compounds suitable for use in the present invention are:

(a) 3-Isothiazolone Compounds

A preferred preservative is an antimicrobial, organic preservative containing 3-isothiazolone groups having the formula:

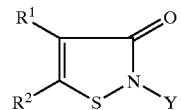

wherein

Y is an unsubstituted alkyl, alkenyl, or alkynyl group of from about 1 to about 18 carbon atoms, an unsubstituted or substituted cycloalkyl group having from about a 3 to about a 6 carbon ring and up to 12 carbon atoms, an unsubstituted or substituted aralkyl group of up to about 10 carbon atoms, or an unsubstituted or substituted aryl group of up to about 10 carbon atoms;

$R^1$ is hydrogen, halogen, or a $(C_1-C_4)$ alkyl group; and
$R^2$ is hydrogen, halogen, or a $(C_1-C_4)$ alkyl group.

Preferably, when Y is methyl or ethyl, $R^1$ and $R^2$ should not both be hydrogen. Salts of these compounds formed by reacting the compound with acids such as hydrochloric, nitric, sulfuric, etc. are also suitable.

This class of compounds is disclosed in U.S. Pat. No. 4,265,899, Lewis et al., issued May 5, 1981, and incorporated herein by reference. Examples of said compounds are: 5-chloro-2-methyl-4-isothiazolin-3-one; 2-n-butyl-3-isothiazolone; 2-benzyl-3-isothiazolone; 2-phenyl-3-isothiazolone, 2-methyl-4,5-dichloroisothiazolone; 5-chloro-2-methyl-3-isothiazolone; 2-methyl-4-isothiazolin-3-one; and mixtures thereof. A preferred preservative is a water-soluble mixture of 5-chloro-2-methyl-4-isothiazolin-3-one and 2-methyl-4-isothiazolin-3-one, more preferably a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Company.

When Kathon® is used as the preservative in the present invention it is present at a level of from about 0.0001% to about 0.01%, preferably from about 0.0002% to about 0.005%, more preferably from about 0.0003% to about 0.003%, most preferably from about 0.0004% to about 0.002%, by weight of the composition.

Other isothiazolins include 1,2-benzisothiazolin-3-one, available under the trade name Proxel® products; and 2-methyl-4,5-trimethylene-4-isothiazolin-3-one, available under the trade name Promexal®. Both Proxel and Promexal are available from Zeneca. They have stability over a wide pH range (i.e., 4–12). Neither contain active halogen and are not formaldehyde releasing preservatives. Both Proxel and Promexal are effective against typical Gram negative and positive bacteria, fungi and yeasts when used at a level from about 0.001% to about 0.5%, preferably from about 0.005% to about 0.05%, and most preferably from about 0.01% to about 0.02% by weight of the usage composition.

(b) Sodium Pyrithione

Another preferred organic sulfur preservative is sodium pyrithione, with water solubility of about 50%. When sodium pyrithione is used as the preservative in the present invention it is typically present at a level of from about 0.0001% to about 0.01%, preferably from about 0.0002% to about 0.005%, more preferably from about 0.0003% to about 0.003%, by weight of the usage composition.

Mixtures of the preferred organic sulfur compounds can also be used as the preservative in the present invention.

Halogenated Compounds

Preferred preservatives for use in the present invention are halogenated compounds. Some non-limiting examples of halogenated compounds suitable for use in the present invention are:

5-bromo-5-nitro-1,3-dioxane, available under the trade name Bronidox L® from Henkel. Bronidox L® has a solubility of about 0.46% in water. When Bronidox is used as the preservative in the present invention it is typically present at a level of from about 0.0005% to about 0.02%, preferably from about 0.001% to about 0.01%, by weight of the usage composition;

2-bromo-2-nitropropane-1,3-diol, available under the trade name Bronopol® from Inolex can be used as the preservative in the present invention. Bronopol has a solubility of about 25% in water. When Bronopol is used as the preservative in the present invention it is typically present at a level of from about 0.002% to about 0.1%, preferably from about 0.005% to about 0.05%, by weight of the usage composition;

1,1'-hexamethylene bis(5-(p-chlorophenyl)biguanide), commonly known as chlorhexidine, and its salts, e.g., with acetic and gluconic acids can be used as a preservative in the present invention. The digluconate salt is highly water-soluble, about 70% in water, and the diacetate salt has a solubility of about 1.8% in water. When chlorohexidine is used as the preservative in the present invention it is typically present at a level of from about 0.0001% to about 0.04%, preferably from about 0.0005% to about 0.01%, by weight of the usage composition.

1,1,1-Trichloro-2-methylpropan-2-ol, commonly known as chlorobutanol, with water solubility of about 0.8%; a typical effective level of chlorobutanol is from about 0.1% to about 0.5%, by weight of the usage composition.

4,4'-(Trimethylenedioxy)bis-(3-bromobenzamidine) diisethionate, or dibromopropamidine, with water solubility of about 50%; when dibromopropamidine is used as the preservative in the present invention it is typically present at a level of from about 0.0001% to about 0.05%, preferably from about 0.0005% to about 0.01% by weight of the usage composition.

Mixtures of the preferred halogenated compounds can also be used as the preservative in the present invention.

Cyclic Organic Nitrogen Compounds

Preferred water-soluble preservatives for use in the present invention are cyclic organic nitrogen compounds. Some non-limiting examples of cyclic organic nitrogen compounds suitable for use in the present invention are:

(a) Imidazolidinedione Compounds

Preferred preservatives for use in the present invention are imidazolidione compounds. Some non-limiting examples of imidazolidinedione compounds suitable for use in the present invention are:

1,3-bis(hydroxymethyl)-5,5-dimethyl-2,4-imidazolidinedione, commonly known as dimethyloldimethylhydantoin, or DMDM hydantoin, available as, e.g., Glydant® from Lonza. DMDM hydantoin has a water solubility of more than 50% in water, and is mainly effective on bacteria. When DMDM hydantoin is used, it is preferable that it be used in combination with a broad spectrum preservative such as Kathon CG®, or formaldehyde. A preferred mixture is about a 95:5 DMDM hydantoin to 3-butyl-2-iodopropynylcarbamate mixture, available under the trade name Glydant Plus® from Lonza. When Glydant Plus® is used as the preservative in the present invention, it is typically present at a level of from about 0.005% to about 0.2% by weight of the usage composition;

N-[1,3-bis(hydroxymethyl)2,5-dioxo-4-imidazolidinyl]-N,N'-bis(hydroxymethyl) urea, commonly known as diazolidinyl urea, available under the trade name Germall II® from Sutton Laboratories, Inc. (Sutton) can be used as the preservative in the present invention. When Germall II® is used as the preservative in the present invention, it is typically present at a level of from about 0.01% to about 0.1% by weight of the usage composition;

N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from (Sutton) can be used as the preservative in the present invention. When imidazolidinyl urea is used as the preservative, it is typically present at a level of from about 0.05% to about 0.2%, by weight of the usage composition.

Mixtures of the preferred imidazolidinedione compounds can also be used as the preservative in the present invention.

(b) Polymethoxy Bicyclic Oxazolidine

Another preferred water-soluble cyclic organic nitrogen preservative is polymethoxy bicyclic oxazolidine, having the general formula:

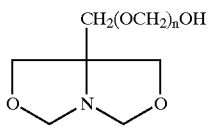

where n has a value of from about 0 to about 5, and is available under the trade name Nuosept® C from Hüls America. When Nuosept® C is used as the preservative, it is typically present at a level of from about 0.005% to about 0.1%, by weight of the usage composition.

Mixtures of the preferred cyclic organic nitrogen compounds can also be used as the preservative in the present invention.

Low Molecular Weight Aldehydes (a). Formaldehyde

A preferred preservative for use in the present invention is formaldehyde. Formaldehyde is a broad spectrum preservative which is normally available as formalin which is a 37% aqueous solution of formaldehyde. When formaldehyde is used as the preservative in the present invention, typical levels are from about 0.003% to about 0.2%, preferably from about 0.008% to about 0.1%, more preferably from about 0.01% to about 0.05%, by weight of the usage composition.

(b) Glutaraldehyde

A preferred preservative for use in the present invention is glutaraldehyde. Glutaraldehyde is a water-soluble, broad spectrum preservative commonly available as a 25% or a 50% solution in water. When glutaraldehyde is used as the preservative in the present invention it is typically present at a level of from about 0.005% to about 0.1%, preferably from about 0.01% to about 0.05%, by weight of the usage composition.

Quaternary Compounds

Preferred preservatives for use in the present invention are cationic and/or quaternary compounds. Such compounds include polyaminopropyl biguanide, also known as polyhexamethylene biguanide having the general formula:

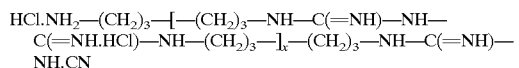

Polyaminopropyl biguanide is a water-soluble, broad spectrum preservative which is available as a 20% aqueous solution available under the trade name Cosmocil CQ® from ICI Americas, Inc., or under the trade name Mikrokill® from Brooks, Inc.

1-(3-Chlorallyl)-3,5,7-triaza-1-azoniaadamantane chloride, available, e.g., under the trade name Dowicil 200 from Dow Chemical, is an effective quaternary ammonium preservative; it is freely soluble in water; however, it has the tendency to discolor (yellow), therefore it is not highly preferred.

Mixtures of the preferred quaternary ammonium compounds can also be used as the preservative in the present invention.

When quaternary ammonium compounds are used as the preservative in the present invention, they are typically present at a level of from about 0.005% to about 0.2%, preferably from about 0.01% to about 0.1%, by weight of the usage composition.

Dehydroacetic Acid

A preferred preservative for use in the present invention is dehydroacetic acid. Dehydroacetic acid is a broad spectrum preservative preferably in the form of a sodium or a potassium salt so that it is water-soluble. This preservative acts more as a biostatic preservative than a biocidal preservative. When dehydroacetic acid is used as the preservative it is typically used at a level of from about 0.005% to about 0.2%, preferably from about 0.008% to about 0.1%, more preferably from about 0.01% to about 0.05%, by weight of the usage composition.

Phenyl and Phenolic Compounds

Some non-limiting examples of phenyl and phenolic compounds suitable for use in the present invention are:

4,4'-diamidino-α,ω-diphenoxypropane diisethionate, commonly known as propamidine isethionate, with water solubility of about 16%; and 4,4'-diamidino-α,ω-diphenoxyhexane diisethionate, commonly known as hexamidine isethionate. Typical effective level of these salts is about 0.0002% to about 0.05% by weight of the usage composition.

Other examples are benzyl alcohol, with a water solubility of about 4%; 2-phenylethanol, with a water solubility of about 2%; and 2-phenoxyethanol, with a water solubility of about 2.67%; typical effective level of these phenyl and phenoxy alcohol is from about 0.1% to about 0.5%, by weight of the usage composition.

Mixtures Thereof:

The preservatives of the present invention can be used in mixtures in order to control a broad range of microorganisms.

Other Optional Ingredients

The compositions of the present invention can comprise a wide range of optional ingredients. The CTFA International Cosmetic Ingredient Dictionary, Sixth Edition, 1995, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

Water-Insoluble Substrates

The compositions of the present invention can also be, optionally, incorporated into a insoluble substrate for application to the skin such as in the form of a treated wipe. Suitable water insoluble substrate materials and methods of manufacture are described in Riedel, "Nonwoven Bonding Methods and Materials," *Nonwoven World* (1987); *The Encyclopedia Americana,* vol. 11, pp. 147–153, vol. 21, pp. 376–383, and vol. 26, pp. 566–581 (1984); U.S. Pat. No. 4,891,227, to Thaman et al., issued Jan. 2, 1990; and U.S. Pat. No. 4,891,228 and U.S. Pat. No. 5,686,088 to Mitra et al., issued Nov. 11, 1997; U.S. Pat. No. 5,674,591; James et al; issued Oct. 7, 1997; all of which are herein incorporated by reference in their entirety.

Methods for Disinfecting and Deodorizing the Skin

The skin sanitizing compositions of the present invention are useful for disinfecting and deodorizing the skin. Generally, the skin disinfection and deodorizing process involves topically applying to the skin a safe and effective amount of a composition of the present invention. The present invention can be used when cleansing processes requiring soap and water are unavailable or inconvenient. The amount of the composition applied, the frequency of application and the period of use will vary widely depending upon the level of disinfection and deodorization desired, e.g., the degree of microbial contamination and/or degree of malodor. Typical amounts of skin sanitizing composition used preferably range from about 0.1 mg/cm$^2$ to about 20 mg/cm$^2$, more preferably from about 0.5 mg/cm$^2$ to about 10 mg/cm$^2$, and most preferably about 1 mg/cm$^2$ to about 5 mg/cm$^2$ of skin area to be cleansed. Preferably, the skin sanitizing compositions of the present invention are used to sanitize and deodorize human and/or animal hands.

The present invention also encompasses the method of applying an effective amount of sanitizing and deodorizing compositions of the present invention onto non-skin surfaces, such as household surfaces, e.g., countertops, kitchen surfaces, food preparing surfaces (cutting boards, dishes, pots and pans, and the like); major household appliances, e.g., refrigerators, freezers, washing machines, automatic dryers, ovens, microwave ovens, dishwashers; cabinets; walls; floors; bathroom surfaces, shower curtains; garbage cans and/or recycling bins, and the like.

Article of Manufacture

The present invention also relates to an article of manufacture comprising a dispensing container containing the deodorizing and sanitizing composition. Said dispensing container can be constructed of any of the conventional material employed in fabricating containers, including, but not limited to: polyethylene; polypropylene; polyacetal; polycarbonate; polyethyleneterephthalate; polyvinyl chloride; polystyrene; blends of polyethylene, vinyl acetate, and rubber elastomer. Other materials can include stainless steel and glass. A preferred container is made of clear material, e.g., polyethylene terephthalate.

Also preferred is an article of manufacture wherein the dispensing container is a spray dispenser. Said spray dispenser is any of the manually activated means for producing a spray of liquid droplets as is known in. A preferred spray container is made of clear material, e.g., polyethylene terephthalate.

EXAMPLES

The skin sanitizing and/or deodorizing compositions in the following illustrate specific embodiments of the skin sanitizing and/or deodorizing compositions of the present invention, but are not intended to be limiting thereof. Other modifications can be undertaken by the skilled artisan without departing from the spirit and scope of this invention.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

Example I

The following are examples of spray sanitizing and deodorizing products (utilizing conventional pump applicator systems) incorporating the compositions of the present invention. The compositions are formed by combining and mixing the ingredients of each column using conventional technology and then applying an appropriate amount of the composition to the skin.

| Ingredient | Example Ia<br>Amount (weight percent) | Example Ib<br>Amount (weight percent) |
|---|---|---|
| Ethanol[1] | 40 | 55 |
| Water | 54.8 | 44 |
| Isopropanol (99%) | 3 | — |
| Hydroxypropyl beta-Cyclodextrin | 1 | 1 |
| Zinc Chloride | 1 | — |
| Benzalkonium Chloride | 0.2 | — |

Example II

The following are example of spray sanitizing and deodorizing products (utilizing conventional pump applicator systems) incorporating the compositions of the present invention. The compositions are formed by combining and mixing the ingredients of each column using conventional technology and then applying an appropriate amount of the composition to the skin.

| Ingredient | Example IIa<br>Amount (weight percent) | Example IIb<br>Amount (weight percent) |
|---|---|---|
| Ethanol[1] | 55 | 55 |
| Water | 40.8 | 41 |
| Isopropanol (99%) | 3 | 3 |
| Hydroxypropyl beta-Cyclodextrin | 1 | — |
| Benzalkonium Chloride | 0.2 | — |
| EPC-K[2] | — | 1 |

Example III.

The following are examples of spray sanitizing and deodorizing products (utilizing conventional pump applicator systems) incorporating the compositions of the present invention. The compositions are formed by combining and mixing the ingredients of each column using conventional technology and then applying an appropriate amount of the composition to the skin.

| Ingredient | Example IIIa<br>Amount (weight percent) | Example IIIb<br>Amount (weight percent) |
|---|---|---|
| Ethanol[1] | 55 | 55 |
| Water | 43.8 | 40 |
| Isopropanol (99%) | — | 3 |
| Hydroxypropyl beta-Cyclodextrin | 0.5 | — |

| Ingredient | Example IIIa Amount (weight percent) | Example IIIb Amount (weight percent) |
|---|---|---|
| alpha-Cyclodextrin | 0.5 | — |
| Methylated beta-Cyclodextrin | — | 1 |
| Benzethonium Chloride | 0.2 | — |
| Zinc Chloride | — | 1 |

The test product was clear and showed improved onion odor control than the control product.

EXAMPLE IV

The following are examples of a spray sanitizing and deodorizing products (utilizing conventional pump applicator systems) incorporating the compositions of the present invention. The compositions are formed by combining and mixing the ingredients of each column using conventional technology and then applying an appropriate amount of the composition to the skin.

| Ingredient | Example IVa Amount (weight percent) | Example IVb Amount (weight percent) |
|---|---|---|
| Ethanol[1] | 40 | 55 |
| Water | 55.4 | 41 |
| Isopropanol (99%) | 3 | 3 |
| Chlorhexidine Gluconate (20% w/v aqueous solution) | 1 | — |
| alpha-Cyclodextrin | 0.4 | 0.5 |
| Hydroxypropyl beta-Cyclodextrin | 0.2 | 0.5 |

EXAMPLE V

The following is an example of a spray sanitizing and deodorizing product (utilizing conventional pump applicator systems) incorporating the compositions of the present invention. The compositions are formed by combining and mixing the ingredients of each column using conventional technology and then applying an appropriate amount of the composition to the skin.

| Ingredient | Amount (weight percent) |
|---|---|
| Ethanol[1] | 55 |
| Water | 41.4 |
| Isopropanol (99%) | 3 |
| alpha-Cyclodextrin | 0.4 |
| beta-Cyclodextrin | 0.2 |

EXAMPLE VI

The following are examples of gel sanitizing and deodorizing compositions of the present invention. The compositions are formed by combining and mixing the ingredients of each column using conventional technology and then applying an appropriate amount of the composition to the skin.

| Ingredient | Example VIa Amount (weight percent) | Example VIb Amount (weight percent) |
|---|---|---|
| Ethanol[1] | 40 | 55 |
| Water | 55.85 | 41.04 |
| Isopropanol | 3 | 3 |
| Glycerin | 0.01 | 0.01 |
| Propylene Glycol | 0.02 | 0.02 |
| alpha-Cyclodextrin | 0.4 | — |
| beta-Cyclodextrin | 0.2 | — |
| Benzalkonium Chloride | 0.2 | — |
| Abscents 2000[3] | — | 0.6 |
| Carbopol 980[4] | 0.22 | 0.22 |
| Aminomethyl Propanol | 0.11 | 0.11 |

EXAMPLE VII

The following are example of a gel sanitizing and deodorizing compositions of the present invention. The compositions are formed by combining and mixing the ingredients of each column using conventional technology and then applying an appropriate amount of the composition to the skin.

| Ingredient | Example VIIa Amount (weight percent) | Example VIIb Amount (weight percent) |
|---|---|---|
| Ethanol[1] | 40 | 55 |
| Water | 54.99 | 41.04 |
| Isopropanol (99%) | 3 | 3 |
| Glycerin | 0.01 | 0.01 |
| Propylene Glycol | 0.02 | 0.02 |
| alpha-Cyclodextrin | 0.4 | 0.4 |
| beta-Cyclodextrin | 0.2 | 0.2 |
| Chlorhexidine Gluconate (20% w/v aqueous solution) | 0.5 | — |
| Carbopol 980[4] | 0.22 | 0.22 |
| Perfume | 0.05 | — |
| Aminomethyl Propanol | 0.05 | 0.11 |

EXAMPLE VIII

The following is an example of a gel sanitizing and deodorizing composition of the present invention. The composition is formed by combining and mixing the ingredients of each column using conventional technology and then applying an appropriate amount of the composition to the skin.

| Ingredient | Amount (weight percent) |
|---|---|
| Ethanol[1] | 55 |
| Water | 40.99 |
| Isopropanol (99%) | 3 |
| Glycerin | 0.01 |
| Propylene Glycol | 0.02 |
| EPC-K[2] | 0.6 |
| Carbopol 980[4] | 0.22 |
| Aminomethyl Propanol | 0.11 |
| Perfume | 0.05 |

EXAMPLE IX

The following is an example of a gel sanitizing and deodorizing composition of the present invention. The composition is formed by combining and mixing the ingredients of each column using conventional technology and then applying an appropriate amount of the composition to the skin.

| Ingredient | Example IXa Amount (Wt. %) | Example IXb Amount (Wt. %) |
|---|---|---|
| Ethanol[1] | 55 | 55 |
| Water | 40.89 | — |
| Isopropanol (99%) | 3 | 3 |
| Glycerin | 0.01 | 0.01 |
| Propylene Glycol | 0.02 | 0.02 |
| Dimethicone Copolyol[5] | 0.05 | 0.05 |
| alpha-cyclodextrinAlpha Cyclodextrin | 0.4 | 0.6 |
| beta-cyclodextrinBeta Cyclodextrin | 0.2 | — |
| Carbopol Ultrez 10[4] | 0.22 | 0.17 |
| Aminomethyl Propanol | 0.11 | 0.08 |
| Perfume | 0.10 | 0.10 |

EXAMPLE X

The following are examples of gel deodorizing compositions of the present invention. The compositions are formed by combining and mixing the ingredients of each column using conventional technology and then applying an appropriate amount of the composition to the skin.

| Ingredient | Example Xa Amount (Wt. %) | Example Xb Amount (Wt. %) | Example Xc Amount (Wt. %) |
|---|---|---|---|
| beta-Cyclodextrin | 1 | — | — |
| Hydroxypropyl beta-Cyclodextrin | — | 0.5 | — |
| Methylated beta-Cyclodextrin | — | — | 0.6 |
| alpha-Cyclodextrin | — | 0.5 | 0.4 |
| Carbopol 980[4] | 0.2 | 0.2 | 0.2 |
| Propylene Glycol | 0.1 | 0.03 | 0.6 |
| Perfume | 0.04 | 0.08 | 0.05 |
| Kathon CG | 3 ppm | 3 ppm | 3 ppm |
| Water | Balance | Balance | Balance |

EXAMPLE XI

The following are examples of gel deodorizing compositions of the present invention. The compositions are formed by combining and mixing the ingredients of each column using conventional technology and then applying an appropriate amount of the composition to the skin.

| Ingredient | Example XIa Amount (Wt. %) | Example XIb Amount (Wt. %) | Example XIc Amount (Wt. %) |
|---|---|---|---|
| beta-Cyclodextrin | 0.5 | — | — |
| Hydroxypropyl beta-Cyclodextrin | — | 1 | — |
| Methylated beta-Cyclodextrin | — | — | 0.5 |
| alpha-Cyclodextrin | 0.5 | — | 0.5 |
| Zinc Chloride | — | 1 | 0.5 |
| Benzalkonium Chloride[6] | 0.03 | — | — |
| Dioctyldimethyl ammonium chloride[7] | — | — | 0.04 |
| Carbopol 980[4] | 0.2 | 0.2 | 0.2 |
| Propylene Glycol | 0.1 | 0.03 | 0.6 |
| Perfume | 0.05 | 0.05 | 0.05 |
| Water | Balance | Balance | Balance |

EXAMPLE XII

The following are examples of gel deodorizing compositions of the present invention. The compositions are formed by combining and mixing the ingredients of each column using conventional technology and then applying an appropriate amount of the composition to the skin.

| Ingredient | Example XIIa Amount (Wt. %) | Example XIIb Amount (Wt. %) | Example XIIc Amount (Wt. %) |
|---|---|---|---|
| beta-Cyclodextrin | 0.2 | — | — |
| Hydroxypropyl beta-Cyclodextrin | — | 0.4 | — |
| Methylated beta-Cyclodextrin | — | — | 1 |
| alpha-Cyclodextrin | 0.4 | 0.6 | — |
| Zinc Chloride | — | — | 0.5 |
| Chlorhexidine chloride | 0.02 | 0.01 | — |
| Didecyldimethyl ammonium chloride[8] | — | — | 0.04 |
| Carbopol 980[4] | 0.2 | 0.2 | 0.2 |
| Polyalkyleneoxide Polysiloxane[9] | 0.1 | — | 0.1 |
| Propylene Glycol | 0.1 | 0.03 | 0.6 |
| Perfume | 0.04 | 0.08 | 0.1 |
| Water | Balance | Balance | Balance |

[1]200 proof
[2]DL-α-tocopheryl-L-ascorbic acid 2-0 phosphate diester or L-ascorbic acid 2-[3,4-dihydro-2,5,7,8-tetramethyl-2-(4,8,12-trimethyltridecyl)-2H-1-benzopyran-6-yl hydrogen phosphate] potassium salt available from Senju Pharmaceutical Co., Ltd. Osaka, Japan.
[3]Organophillic molecular sieve from UOP.
[4]Crosslinked polyacrylic acid available from B.F. Goodrich (the Carbopol thickening/gelling agents are processed before incorporation into the exemplified formulations with NaOH/KOH to provide compatible pH (pH from about 5 to about 9, preferably about 6 to about 8).
[5]Dow Corning Resin Modifier Q2-5220
[6]Barquat 4250 available from Lonza, Inc. (Fair Lawn, N.J.)
[7]Bardac 2050 available from Lonza, Inc. (Fair Lawn, N.J.)
[8]Bardac 22 available from Lonza, Inc. (Fair Lawn, N.J.)
[9]Silwet L-7600

What is claimed is:

1. A method of deodorizing human hands, said method comprising topically applying to the hands from about 0.1 mg/cm2 to about 20 mg/cm2 of a deodorizing gel composition, said deodorizing gel composition comprising:
    (a) from about 0.1% to about 10% of a cyclodextrin;
    (b) from 0.01% to about 10% by weight of a thickener;
    (c) from about 0.5% to about 50% by weight of an emollient;
    (d) from about 10% to about 70% by weight of water,
    wherein the composition is in the form of a gel.
2. A method according to claim 1, wherein the cyclodextrin is selected from the group consisting of water-soluble, uncomplexed cyclodextrin; water-soluble, uncomplexed cyclodextrin derivatives; or mixtures thereof.

3. A method according to claim 2, wherein the water-soluble, uncomplexed cyclodextrin derivatives are selected from the group consisting of methyl substituted cyclodextrins, ethyl substituted cyclodextrins, hydroxyalkyl substituted cyclodextrins, (hydroxyalkyl)alkylenyl substituted cyclodextrins, branched cyclodextrins, cationic cyclodextrins, quaternary ammonium cyclodextrins, anionic cyclodextrins, amphoteric cyclodextrins, cyclodextrins wherein at least one glucopyranose unit has a 3-6-anhydro-cyclomalto structure, and mixtures thereof.

4. A method according to claim 2, wherein the water-soluble, uncomplexed cyclodextrin is selected from the group consisting of beta-cyclodextrins and its derivatives, alpha-cyclodextrin and its derivatives, gamma-cyclodextrin and its derivatives, and mixtures thereof.

5. A method according to claim 4, wherein the water-soluble, uncomplexed cyclodextrin is selected from the group consisting of alpha-cyclodextrin, methylated alpha-cyclodextrin, beta-cyclodextrin, methylated beta-cyclodextrin, hydroxyethyl alpha-cyclodextrin, hydroxyethyl beta-cyclodextrin, hydroxypropyl alpha-cyclodextrin, hydroxypropyl beta-cyclodextrin, beta-cyclodextrin glycerol ether, and mixtures thereof.

6. A method according to claim 5, wherein the water-soluble, uncomplexed cyclodextrin is selected from the group consisting of alpha-cyclodextrin, beta-cyclodextrin arid mixtures thereof.

7. A method according to claim 5, wherein the cyclodextrin is a mixture of alpha-cyclodextrin and beta-cyclodextrin.

8. A method according to claim 5, wherein the cyclodextrin is selected from the group consisting of hydroxypropyl beta-cyclodextrin, methylated beta-cyclodextrin and mixtures thereof.

9. A method according to claim 5, wherein the cyclodextrin is a mixture of two or more cyclodextrins selected from the group consisting of alpha-cyclodextrin, methylated beta-cyclodextrin, methylated alpha-cyclodextrin, hydroxypropyl alpha-cyclodextrin and hydroxypropyl beta-cyclodextrin.

10. A method according to claim 7, wherein the thickener represents from about 0.1% to about 5% by weight of the deodorizing gel composition and is selected from the group consisting of sodium alginate, xanthan gum, quince seed extract, tragacanth gum, starch, hydroxyethyl cellulose, methyl cellulose, carboxymethyl cellulose, hydroxy propylmethyl cellulose, polyvinylpyrrolidone, polyvinylalcohol, guar gum, hydroxypropyl guar gum, soluble starch, cationic celluloses, cationic guars, carboxyvinyl polymers, polyacrylic acid, crosslinked polyacrylic acid, polyvinyl alcohol polyacrylic acid polymers, polymethacrylic acid polymers, polyvinyl acetate polymers, polyvinyl chloride polymers, polyvinylidene chloride polymers, aluminium silicates, bentonites, hydrophobically modified celluloses, and mixtures thereof.

11. A method according to claim 10, wherein the thickener is selected from the group consisting of polyacrylic acid, crosslinked polyacrylic acid and mixtures thereof.

12. A method according to claim 2, wherein the deodorizing gel composition further contains a from about 0.1% to about 10%, by weight of a water-soluble metallic salt selected from the group consisting of water-soluble zinc salts, water-soluble copper salts, and mixtures thereof.

13. A method according to claim 12, wherein the metallic salt is selected from the group consisting of zinc chloride, zinc gluconate, zinc lactate, zinc maleate, zinc salicylate, zinc sulfate, copper chloride, copper gluconate, arid mixtures thereof.

14. A method according to claim 13, wherein the metallic salt is zinc chloride and represents from about 0.2% to about 5% by weight of the deodorizing gel.

15. A method according to claim 1, wherein the deodorizing gel composition further comprises from about 0.001% to about 1% by weight of a perfume, and wherein the weight ratio of the odor controlling agent to the perfume is greater than about 10:1.

16. A method according to claim 15, wherein the deodorizing gel composition comprises from about 0.005% to about 0.5% by weight of the perfume, and wherein the weight ratio of the odor controlling agent to the perfume is greater than about 40:1.

17. A method according to claim 2, wherein the deodorizing gel composition further comprises from about 0.001% to about 0.5% by weight a perfume, and wherein at least about 50% by weight of the perfume ingredients in the perfume have a ClogP of less than about 3.5.

18. A method according to claim 17, wherein the perfume is selected from the group consisting of allyl amyl glycolate, allyl caproate, amyl acetate, amyl propionate, anisic aldehyde, anisyl acetate, anisole, benzaldehyde, benzyl acetate, benzyl acetone, benzyl alcohol, benzyl formate, benzyl iso valerate, benzyl propionate, beta gamma hexenol, calone, camphor gum, laevo-carveol, d-carvone, laevo-carvone, cinnamic alcohol, cinnamyl acetate, cinnamic alcohol, cinnamyl formate, cinnamyl propionate, cis-jasmone, cis-3-hexenyl acetate, coumarin, cuminic alcohol, cuminic aldehyde, Cyclal C, cyclogalbanate, dihydroeuginol, dihydro isojasmonate, dimethyl benzyl carbinol, dimethyl benzyl carbinyl acetate, ethyl acetate, ethyl aceto acetate, ethyl amyl ketone, ethyl anthranilate, ethyl benzoate, ethyl butyrate, ethyl cinnamate, ethyl hexyl ketone, ethyl maltol, ethyl-2-methyl butyrate, ethyl methylphenyl glycidate, ethyl phenyl acetate, ethyl salicylate, ethyl vanillin, eucalyptol, eugenol, eugenyl acetate, eugenyl formate, eugenyl methyl ether, fenchyl alcohol, flat acetate (tricyclo decenyl acetate), fructone, frutene (tricyclo decenyl propionate), geraniol, geranyl oxyacetaldehyde, heliotropin, hexenol, hexenyl acetate, hexyl acetate, hexyl formate, hinokitiol, hydratropic alcohol, hydroxycitronellal, hydroxycitronellal diethyl acetal, hydroxycitronellol, indole, isoamyl alcohol, iso cyclo citral, isoeugenol, isoeugenyl acetate, isomenthone, isopulegyl acetate, isoquinoline, keone, ligustral, linalool, linalool oxide, linalyl formate, lyral, menthone, methyl acetophenone, methyl amyl ketone, methyl anthranilate, methyl benzoate, methyl benzyl acetate, methyl cinnamate, methyl dihydrojasmonate, methyl eugenol, methyl heptenone, methyl heptine carbonate, methyl heptyl ketone, methyl hexyl ketone, methyl isobutenyl tetrahydropyran, methyl-N-methyl anthranilate, methyl beta naphthyl ketone, methyl phenyl carbinyl acetate, methyl salicylate, nerol, nonalactone, octalactone, octyl alcohol (octanol-2), para-anisic aldehyde, para-cresol, para-cresyl methyl ether, para hydroxy phenyl butanone, para-methoxy acetophenone, para-methyl acetophenone, phenoxy ethanol, phenoxyethyl propionate, phenyl acetaldehyde, phenylacetaldehyde diethyl ether, phenylethyl oxyacetaldehyde, phenyl ethyl acetate, phenyl ethyl alcohol, phenyl ethyl dimethyl carbinol, prenyl acetate, propyl butyrate, pulegone, rose oxide, safrole, terpineol, vanillin, viridine, allyl heptoate, amyl benzoate, anethole, benzophenone, carvacrol, citral, citronellol, citronellyl nitrile, cyclohexyl ethyl acetate, cymal, 4-decenal, dihydro isojasmonate, dihydro myrcenol, ethyl methyl phenyl glycidate, fenchyl acetate, florhydral, gamma-nonalactone, geranyl formate, geranyl nitrile, hexenyl isobutyrate, alpha-ionone, isobornyl acetate, isobutyl benzoate, isononyl alcohol, isomenthol, para-isopropyl phenylacetaldehyde, isopulegol, linalyl acetate, 2-methoxy naphthalene, menthyl acetate, methyl chavicol, musk ketone, beta naphthol methyl ether, neral, nonyl aldehyde, phenyl heptanol, phenyl hexanol, terpinyl acetate, Veratrol, yara—yara, and mixtures thereof.

19. A method according to claim 18, wherein up to about 10% by weight of the perfume are perfume ingredients selected from the group consisting of ambrox, bacdanol, benzyl salicylate, butyl anthranilate, cetalox, damascenone, alpha-damascone, gamma-dodecalactone, ebanol, herbavert, cis-3-hexenyl salicylate, alpha-ionone, beta-ionone, alpha-isomethylionone, lilial, methyl nonyl ketone, gamma-undecalactone, undecylenic aldehyde, and mixtures thereof.

20. A method according to claim 1, wherein the emollient is selected from the group consisting of petrolatum, mineral oil, micro-crystalline wax, polyalkene, paraffin, cerasin, ozokerite, polyethylene and perhydrosqualene, dimethicones, alkyl siloxane, polymethylsiloxane, methylphenylpolysiloxane, and mixtures thereof.

21. A method according to claim 1, wherein the deodorizing gel composition further comprises a skin sensate.

22. A method according to claim 21, wherein the skin sensate is selected from the group consisting of menthol, eucalyptus, 3-1-menthoxy propane-1,2-diol, N-substituted-p-menthane-3-carboxamides, acyclic carboxamides and mixtures thereof.

23. A method according to claim 1 wherein the deodorizing gel composition further comprises from about 0.01% to about 5% by weight of a surfactant.

24. A method according to claim 23, wherein the surfactant is selected from the group consisting of polyalkyleneoxide polysiloxanes, block copolymers of ethylene oxide and propylene oxide, and mixtures thereof.

25. A method according to claim 1, wherein the deodorizing gel composition is clear.

26. A method according to claim 1, wherein the deodorizing gel composition contains no sanitizing agent.

* * * * *

UNITED STATES PATENT AND TRADEMARK OFFICE
CERTIFICATE OF CORRECTION

PATENT NO.   : 6,656,456 B2
DATED        : December 2, 2003
INVENTOR(S)  : Michael Thomas Dodd et al.

It is certified that error appears in the above-identified patent and that said Letters Patent is hereby corrected as shown below:

Column 31,
Line 27, "arid" should read -- and --.
Line 40, "7" should read -- 1 --.
Line 66, "arid" should read -- and --.

Column 32,
Line 37, "flat" should read -- flor --.

Signed and Sealed this

Seventeenth Day of August, 2004

JON W. DUDAS
*Acting Director of the United States Patent and Trademark Office*